United States Patent [19]
Errico

[11] Patent Number: 6,163,727
[45] Date of Patent: Dec. 19, 2000

[54] HOOK SHAPED SPINAL CORD ELECTRODE ASSEMBLY

[75] Inventor: Thomas J. Errico, Summit, N.J.

[73] Assignee: Electro Core Technologies, LLC

[21] Appl. No.: 09/323,621

[22] Filed: Jun. 1, 1999

[51] Int. Cl.[7] .................................................. A61N 1/05
[52] U.S. Cl. ............................................................ 607/117
[58] Field of Search ................................... 607/116, 117

[56] References Cited

U.S. PATENT DOCUMENTS

| | | | |
|---|---|---|---|
| 5,423,877 | 6/1995 | Mackey | 607/117 |
| 6,066,165 | 5/2000 | Racz | 607/117 |

Primary Examiner—Scott M. Getzow
Attorney, Agent, or Firm—Joseph P. Errico, Esq.

[57] ABSTRACT

A spinal electrode for use in spinal cord stimulation included in a laminar hook so that displacement of the electrode cannot easily occur by normal bodily motion as is a failure mechanism of prior electrode designs. The electrical contacts of the electrode are disposed on the underside of the blade portion of the hook. The head of the hook, which seats above the lamina, is coupled either to the spinous process, or to the head of a hook which is positioned in an opposing orientation. The head of the hook in one embodiment includes a hole through which a wire may be passed to tie the hook to the spinous process, or to the other hook. In a second embodiment, the head of the hook has a notch formed in it so that it may receive an elastomeric band which is used to couple the head of the hook to the spinous process, or to another hook.

12 Claims, 2 Drawing Sheets

HOOK SHAPED SPINAL CORD ELECTRODE ASSEMBLY

BACKGROUND OF THE INVENTION

1. Field of the Invention

This invention relates generally to a device used in the treatment of neurological disorders, especially pain and motor disfunction by electro-stimulation of nerve fibers of the spinal cord, and more particularly to a novel combined assembly of an electrode and lamina hook which is more reliable in maintaining the position of the electrode relative to the target fibers of the spinal cord.

2. Description of the Prior Art

The use of electrical stimulation for the purposes of alleviating pain and the treatment of other neurological afflictions has been utilized for a number of years, and in many instances has become the standard of care. In new applications, as well, electrical stimulation of components of the nervous system continues to show significant therapeutic promise.

More particularly, in the spine, the original approach to electrical stimulation was to place multiple electrical leads directly onto the dura around the spinal cord. In such a procedure, the laminae of a sequence of vertebrae were removed so that the leads could be placed in a spaced apart relation along the central posterior axis of the spinal cord. This approach required a substantially invasive procedure in which bones and tissue were displaced or removed. In addition, the high frequencies of electrode migration from the target site or sites rendered the entire procedure suspect.

Subsequent iterations of spinal cord stimulation devices were implanted much less invasively, generally by percutaneous positioning. The first generations of this approach were immediately advantageous over the prior methods, insofar as they were carried out using local anesthetic as the electrodes were guided into position with the use of a fluoroscope. These early non-invasive procedures continued to use single lead electrodes, thus requiring a plurality of separate implantations. In addition, the leads would still easily become dislodged and migrate from the desired treatment site, usually becoming ineffective, but sometimes having actively negative effects on other nerves. These limitations and failures associated with multiple implantations of single lead electrodes briefly caused a reversion to the older, more invasive approach.

In an attempt to unify the multiple leads necessary for spinal cord stimulation into a single electrode, thereby attempting to bring the state of the art back to non-invasive procedures, designs from the cardiovascular art, i.e. pacemakers, et al., were modified for use in the spine. Multiple lead electrodes had been used in the cardiovascular field for some time, and were generally designed to provide stimulation to a variety of points on the surface of the heart. The modifications of these leads included strengthening the both the leads and the structure containing the leads for the stresses of the spine, reducing the diameter of the leads to a size more appropriate for use in the spine, and alternatively providing either a removeable or permanent rigid wire within the electrode to enhance placement. Unfortunately, while eliminating some of the causes associated with electrode migration, and reducing the number of electrodes which could migrate, the advances did not address the fundamental inability to fix the electrode at the appropriate location. This problem has been, and continues to be a significant drawback to the use of spinal cord stimulation in the regular treatment of pain.

Accordingly, it is an object of the present invention to provide a spinal cord stimulator assembly which reduces the incidence and complications associated with the migration of the electrode.

SUMMARY OF THE INVENTION

The preceding objects are provided in the present invention, which comprises new and novel embodiments of electrode and lamina attachment devices for use in spinal cord stimulation, and which may be used in conjunction with standard and/or advanced electrical signal sources. More particularly, a variety of different embodiments of the present invention are contemplated, exemplary ones of which are disclosed herein, including various electrode and lamina hook combinations.

In a first embodiment, the present invention comprises an elongate wire lead portion which couples to an elastomeric hook element having a series of electrical terminal pads on the underside of the blade thereof. More specifically, the combined hook and electrode structure comprises a plurality of wire leads encased in an elongate elastomeric sheath. This sheath may be of any suitable cross-sectional shape, however, a cylindrical tube is preferred. It is also necessary that the material comprising the sheath be electrically insulating, and that each wire be insulated relative to each other and to the exterior of the sheath. The wires are also preferably wound into individual helices so that flexible motion of the sheath does not damage the wires. The proximal end of the sheath includes a series of electrical contacts, each coupled to an individual wire lead. These contacts are provided so that the electrode may be easily coupled to an electric signal source (voltage sources) and so that a separate voltage may be applied to each wire lead individually.

At the distal end of the elastomeric sheath is a lamina hook which includes an upper head portion and a lower blade portion. The hook further includes an interior structural member, formed of plastic or other suitably rigid material, which maintains the integrity of the hook shape. The exterior surface of the hook, however, is covered with the same elastomeric material as the sheath.

The head of the hook includes a hole, which extends transverse to the direction of the blade and to the vertical axis of the head itself. This hole is provided to receive a surgical wire, and more particularly, a wire which is used to secure the hook portion to the lamina.

The sheath portion of the electrode joins the hook at the head thereof, and the wire leads extend down from the head of the hook to the blade. Preferably, the wires are disposed within the elastomeric material coating the hook, however, provided the interior structural material which provides structural integrity for the hook is nonconducting, the wires may be positioned between the elastomeric material and the structural material.

The blade is the portion of the hook which seats beneath the lamina, such that the member cups the lateral edge of the lamina with the blade seated in the spinal canal, directly above the spinal cord. The undersurface of the blade includes a series of terminal pads which are coupled to the wire leads, thereby in electrical communication with the electrical contacts at the proximal end of the sheath. Each terminal pad is coupled to a corresponding one of the electrical contacts of the proximal end of the sheath, whereby an individual potential may be provided to each of the terminal pads of the blade of the hook.

Surgical implantation and use of this device begins with the preparation of the particular site which is to receive the electrode assembly. This generally requires the clearing of some soft tissue from around the target lamina. The blade of the hook is then inserted under the lamina, into the spinal canal, at the desired position such that the terminal pads are located directly adjacent to the nerve fibers which are to be subject to the applied potential field. An electrical signal source generator is then coupled to the proximal end of the electrode sheath and a series of applied potentials may be provided to the terminal pads. The source generator may be implanted, or the wire leads may extend transcutaneously to an external power source. In either event, the electrode sheath extends long the spine outside the spinal canal, with only the blade of the hook extending into this region.

In a second embodiment, a pair of electrode hooks are utilized on either side of the same lamina (or adjacent laminae) such that the two hooks form a joined clamp around the outer edges of the lamina to secure themselves and the terminal pads thereof in position. More particularly, each of the hook elements of this second embodiment is structurally similar to the first embodiment disclosed above in that each comprises an elongate and flexible elastomeric sheath portion which contains a plurality of wound wire leads coupled to electrical contacts at the proximal end of the sheath. The hook portions of the electrodes include a structural member which supplies rigidity to the head and blade portions. An elastomeric covering is also provided to the hook, and the wires of the sheath extend into the head of the hook and down to terminal pads disposed on the underside of the blade portions of the hook. Again, each terminal pad is coupled to a corresponding one electrical contact of the proximal end of the sheath by a corresponding one wire lead.

Unlike the electrode hook combination of the first embodiment, in which the hook is coupled to the lamina against which it is seated (and more particularly to the spinous process of the lamina), the present embodiments are coupled to one another. While the tranverse wire hole of the first embodiment could be utilized to permit coupling of those hooks to one another, this rigid sugical wire would immobilize the sequence of vertebra coupled by the hooks. It is, therefore, preferable that the heads of the hooks of this embodiment be coupled together in a different manner. The desired coupling technique involves an elastomeric band which slips over the heads of the two hooks and prevents them from backing out of their positions, but does not otherwise inhibit motion of the spine. In order to facilitate the coupling of the ban to the head of the hook in a manner which minimizes the occurance of slippage, the head of the hook may include a notch into which the elastomeric band seats.

It shall be understood that the specific disposition of terminal pads on the underside of the blade portions of either of these embodiments may be selected from a nearly infinite variety. Four terminal pads in a linear series, a square pattern, or staggered pairs are three variations which may be most applicable.

THE DETAILED DESCRIPTION OF THE PREFERRED EMBODIMENTS

While the present invention will be described more fully hereinafter with reference to the accompanying drawings, in which particular embodiments are shown, and with respect to methods of implantation, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
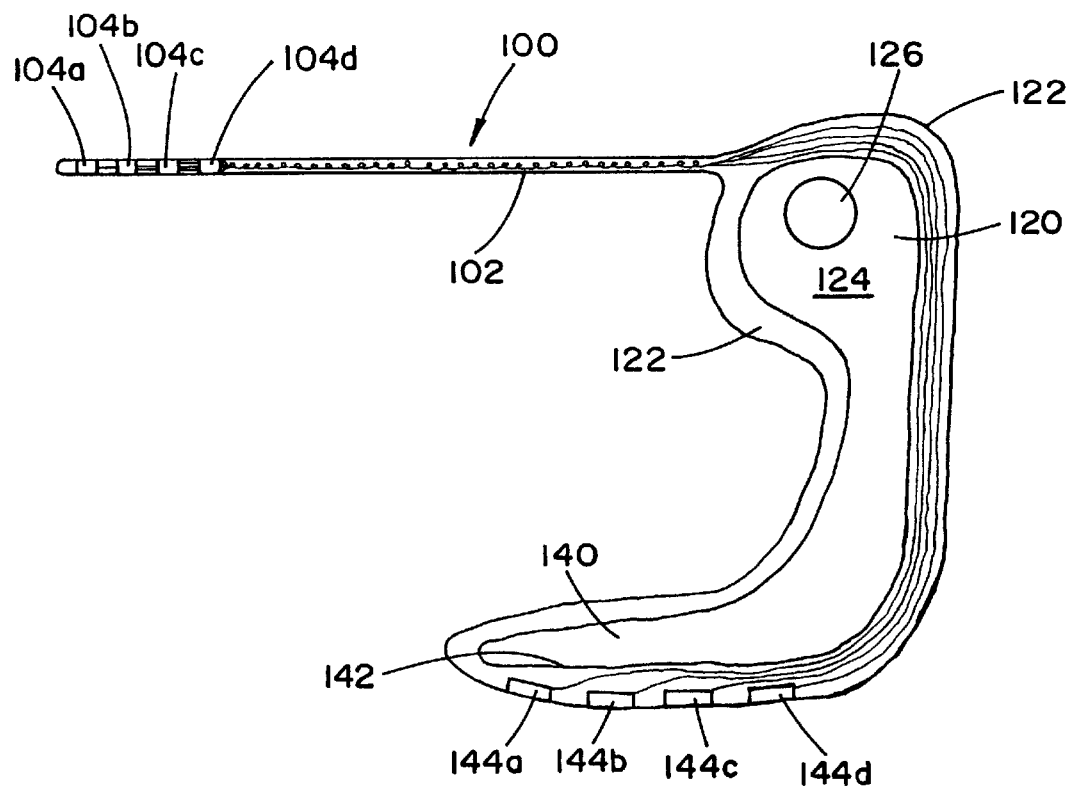
FIG. 1 is a side cross-section view of an electrode and lamina hook combination which is an aspect of the present invention.

Referring now to FIG. 1, the first embodiment of the present invention comprises a spinal cord stimulation electrode being shaped in the form of a hook. The undersurface of the blade of the hook includes the active electrical contacts. In addition, the head of the hook includes a through hole such that it may receive, therethrough, a standard surgical wire, which may be utilized to secure the electrode structure to the lamina (the spinous process). This secure fixation prevents the electrode from translating or sliding in a way which moves the electrical contacts away from their ideal disposition which is adjacent to the target nerve fiber or fibers.

More particularly, this embodiment of the present invention comprises three distinct elements which shall be described in detail: (1) the flexible sheath 100 which contains the wire leads, and connects the hook shaped electrode to the power source; (2) the head 120 of the hook, which includes the through hole used for coupling the hook to the spinous process; and (3) the blade portion 140, which seats under the lamina and includes the active electrical contacts on the undersurface thereof.

First, with respect to the sheath 100, the present invention includes a plurality of thin wires 102 which are wound in tight helices, but which are insulated from one another such that they each may carry a different electrical potential. The wires 102 are encased in the sheath 100 which is comprised of an elastomeric, insulating, and flexible material so that the structure remains easily manipulateable in the axial as well as transverse directions and so that destructive deformation of the wires 102 is minimized in conjunction with movement. (Although not shown, the wound structure may permit the inclusion of a rigid wire, which may be slideably inserted or removed from the electrode by the surgeon, and which provides the rigidity which may be necessary during initial implantation.) Each of said wire leads 102 is shown as coupled to a series of corresponding individual terminals 104a–d located at the proximal end of the sheath 100. The terminals 104a–d and the portion of the elastomeric sheath 100 which contains them are shown as a continuous cylinder (as is the rest of the sheath). That is, the proximal end of the sheath is cylindrical and the terminals 104a–d are circumferential contacts extending around the sheath, each forming an electrical contact band. The terminal portion of the electrode may, however, be flattened out, forming a thin ribbon-like structure. (The second embodiment, shown in FIG. 2, includes such a conformation.) In either case, the terminals 104a–d are spaced apart from one another so that they are in electrical iolation from one another.

The head 120 of the hook portion of this embodiment is preferably also covered in an elastomeric material 122, thus making it insulated and non-damaging to the surrounding tissues. The internal structure 124 of the head (and the entirety of the hook), shown here as an interior shape having the same conformation is the hook, only smaller, comprises a rigid material, for example a hard plastic. It is preferred that this rigid material not be conducting, although it is possible for the material to be metal, so long as precautions are taken to ensure that the wire leads 102 do not make electrical contact with this material 124. The head also includes an overall conformation which enhances the coupling of the head 120 to the spinous process, or another bony structure. In the present embodiment, this conformation comprises a hole 126 which extends transverse to the axis of the head and transverse to the axis of the blade 140 (see below).

The sheath 100 joins the hook at the head 120. More particularly, the wire leads 102 from the sheath 100 enter into the head 120 of the hook and extend between the rigid structural material 124 and the elastomeric and insulating covering 122 (the wires 102 being either insulated themselves, or traveling through only the elastomeric material in the case where the structural material 124 is a conductor such as a metal).

The blade 140 of the hook is an elongate extending member which is joined to the head 120 in such a way as to permit the hook to cup the lateral edge of the lamina of a human vertebral bone. The wire leads 102 extend axially along the underside 142 of the blade and couple to electrical contacts 144*a–d*. In the present embodiment, the contacts 144*a–d* are shown as being linearly disposed along the axis of the blade 140. Each of the contacts 144*a–d* is connected by the corresponding wire lead 102 to individual ones of the terminals 104*a–d*, and are thereby coupleable to different voltages within the potential source. This contacts and their relative position determine the distribution of electric field potential through the tissue against which the underside of the blade is placed. This current causes the disruption of pain signals in the targt nerve roots, thus alleviating pain or other suitably treatable disorder.

Figure 2:
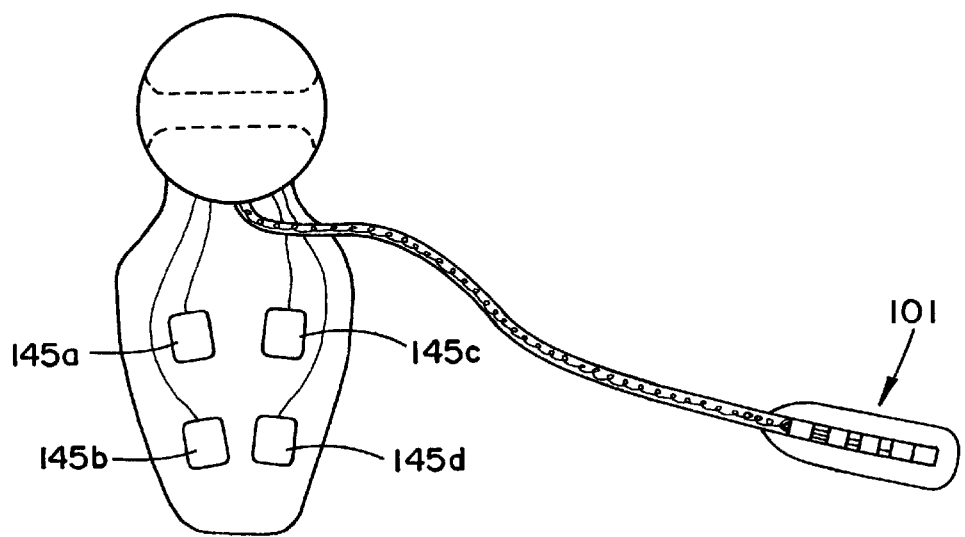
FIG. 2 is a top phantom view of an electrode and lamina hook combination similar to the one shown in FIG. 1, having a different terminal pad disposition.

Referring now to FIG. 2, a top view of a variation of the embodiment described in conjunction with FIG. 1 is provided. This variation differs in only two minor features: the distribution of the electrical contacts on the undersurface of the blade and the form of the terminals at the proximal end of the sheath. More particularly, electrical contacts 145*a–d* are disposed on the underside of the blade 140 at the vertices of a square. It shall be readily understood that the distribution of the electrical contacts on the blade is entirely subject to the specific anatomical spacing of the target nerve fibers. With respect to the terminal portion of the sheath 101, and more particularly, the proximal en of the sheath 101 in general, this embodiment shows that the sheath need not be cylindrical. In the present illustration, the terminal portion of the sheath is ribbon-like, having planar terminals which are circular.

Figure 3:
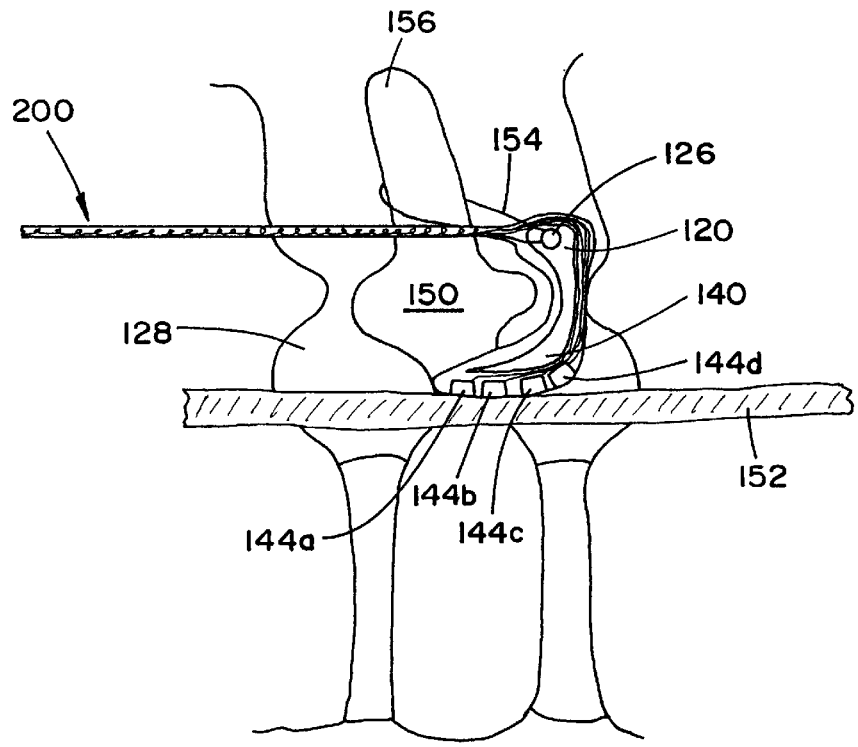
FIG. 3 is a side perspective view of the electrode and lamina hook combination shown in FIGS. 1 and 2, coupled to the lamina of a human spine.

Referring now to FIG. 3, in which a hook shaped electrode of the type shown in FIG. 1 is shown in a side perspective view, having been implanted into the spinal column of a patient, the method of implantation and particular features of the present invention associated with the coupling of the hook to the laminar bone is descrbed. The blade 140 of the invention is intended to be inserted between the laminae 150 of two adjacent vertebrae such that the active electrical contacts 144*a–d* on the undersurface thereof are disposed against the dura of the spinal cord 152, and adjacent to the target nerve fibers. This is the desired position for the electrode to apply the most direct electric field to the target nerves. A wire 154 is then inserted through the hole 126 in the head 120 and tied around the spinous process 156. This action secures the blade 140 of the electrode from backing out of spinal canal 128.

Figure 4:
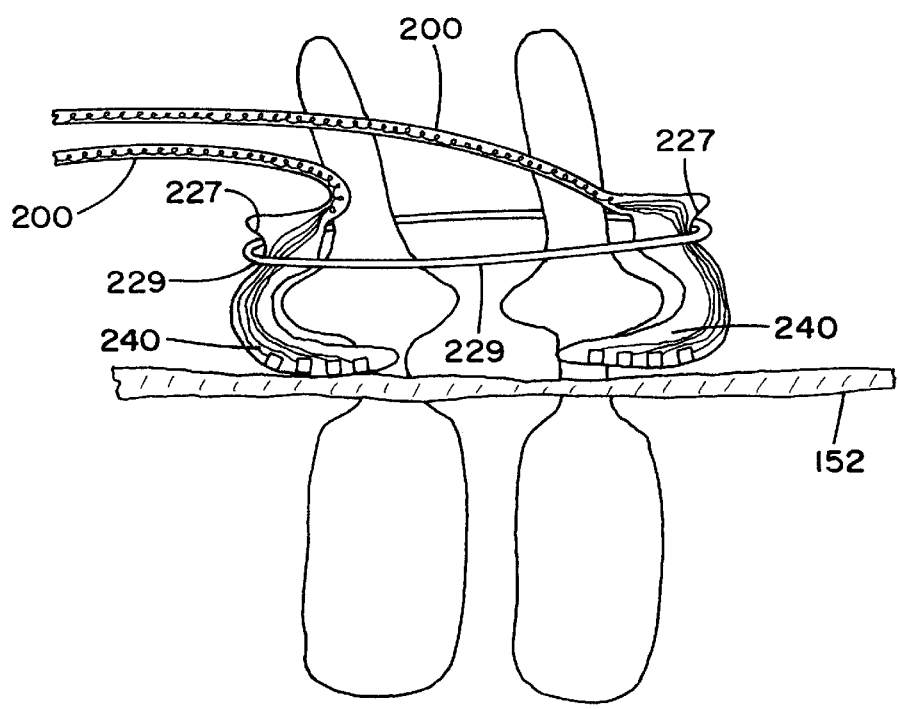
FIG. 4 is a side perspective view of a second embodiment of the electrode and lamina hook combination which is an aspect of the present invention, coupled to the laminae of a human spine.

Referring now to FIG. 4, and important alternative embodiment of this invention is shown in a side perspective view having a pair of opposing hook electrodes mounted to adjacent lamina. In this embodiment the sheath 200 and blade 240 portions of the electrodes are constructed identically to those of the embodiment shown in FIG. 1. The critical difference with this embodiment is that the pair of hooks are coupled together across a sequence of vertebrae. More particularly, the heads of the hooks are constructed having a notch 227 which is designed to receive a coupling means. This coupling means could be a rigid wire, however, this would immobilize the associated vertebrae. As retained flexibility and range of motion are desirable features associated with any surgical procedure, the use of an elastomeric band 229 is warranted.

As with the previous embodiments described, the blade of the hook electrode is advanced into the spinal canal such that the undersurface of the blade, which comprises the electrical contacts, seats directly above the targted fibers of the spinal cord. The proximal ends of the sheath containing the wire leads is coupled to a potential source (preferably one having the abiliuty to apply individual potentials to each lead). The heads of the opposing hooks are then coupled together by the elastomeric band, and are thereby retained in proper position.

While there has been described and illustrated specific embodiments of new and novel electrical stimulation implant devices, it will be apparent to those skilled in the art that variations and modifications are possible without deviating from the broad spirit and principle of the present invention which shall be limited solely by the scope of the claims appended hereto.

What is claimed is:

1. A spinal stimulation electrode comprising:
    at least one wire lead having a proximal end and a distal end, said proximal end being coupleable to an electrical signal generator;
    a lamina hook having a head and a blade, said blade having an undersurface which seats adjacent to the spinal cord when said lamina hook is mounted to a lamina of a spine;
    said at least one wire lead being coupled to said lamina hook at the distal end thereof; and
    said lamina hook having at least one electrical contact formed on said underside of said blade, said electrical contact being electrically coupled to said at least wire lead such that when the hook is disposed on a lamina of a spine, with the blade seated adjacent to the spinal cord, the application of an electrical signal to the proximal end of the at least one wire lead causes an electric potential to be applied to the spinal cord.

2. The spinal stimulation electrode as set forth in claim 1, wherein said at least one wire lead comprises a plurality of wire leads.

3. The spinal stimulation electrode as set forth in claim 2, wherein said at least one electrical contact comprises a plurality of electrical contacts.

4. The spinal stimulation electrode as set forth in claim 1, wherein the at least one wire lead is encased in an insulating and flexible elastomeric sheath.

5. The spinal stimulation electrode as set forth in claim 1, wherein the lamina hook includes a coating of an insulating and flexible elastomeric material.

6. The spinal stimulation electrode as set forth in claim 1, wherein the head includes means for being coupled to a bone of the spine to which the hook is mounted.

7. The spinal stimulation electrode as set forth in claim 6, wherein the means for being coupled to a bone comprises a hole through which a wire may be passed and tied to the bone.

8. The spinal stimulation electrode as set forth in claim 6, wherein the means for being coupled to a bone comprises a notch for receiving a band.

9. A spinal stimulation electrode comprising:

at least two lamina hooks, each having a head and a blade, said blade having an undersurface which seats adjacent to the spinal cord when said lamina hook is mounted to a lamina of a spine;

said at least two lamina hooks being mounted to at least two different laminae, and being oriented on relative lateral outside surfaces said at least two different laminae;

at least two wire leads having proximal ends and distal ends, said proximal ends being coupleable to electrical signal generators;

at least one of said at least two wire leads being coupled to each of said lamina hooks at the distal end thereof; and said lamina hooks each having at least one electrical contact formed on said underside of said blade, said electrical contact being electrically coupled to said at least one wire lead such that when the hook is disposed on a lamina of a spine, with the blade seated adjacent to the spinal cord, the application of an electrical signal to the proximal end of the at least one wire lead causes an electric potential to be applied to the spinal cord.

10. The spinal stimulation electrode as set forth in claim 9, further including means for coupling said at least two lamina hooks together.

11. The spinal stimulation electrode as set forth in claim 10, wherein said means for coupling said at least two lamina hooks together comprises through holes formed in the heads of each hook and a surgical wire looped through the holes.

12. The spinal stimulation electrode as set forth in claim 10, wherein said means for coupling said at least two lamina hooks together comprises an elastomeric band formed about the heads of said hooks.

\* \* \* \* \*